United States Patent
Arcand et al.

(10) Patent No.: US 8,933,416 B2
(45) Date of Patent: Jan. 13, 2015

(54) CATHETER INSERTION STERILIZATION

(75) Inventors: Benjamin Arcand, Minneapolis, MN (US); Joseph E. Hale, Lake Elmo, MN (US); Nikhil Murdeshwar, Maple Grove, MN (US); Bryan Rolfes, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 182 days.

(21) Appl. No.: 13/319,875

(22) PCT Filed: May 11, 2010

(86) PCT No.: PCT/US2010/034362
§ 371 (c)(1),
(2), (4) Date: Mar. 15, 2012

(87) PCT Pub. No.: WO2010/132429
PCT Pub. Date: Nov. 18, 2010

(65) Prior Publication Data
US 2012/0161032 A1    Jun. 28, 2012

Related U.S. Application Data

(60) Provisional application No. 61/177,042, filed on May 11, 2009.

(51) Int. Cl.
| | | |
|---|---|---|
| *G01N 23/00* | (2006.01) |
| *G01N 21/00* | (2006.01) |
| *A61M 25/01* | (2006.01) |
| *A61L 2/00* | (2006.01) |
| *A61L 2/10* | (2006.01) |
| *A61N 5/06* | (2006.01) |
| *A61M 25/06* | (2006.01) |
| *A61M 39/02* | (2006.01) |

(52) U.S. Cl.
CPC .............. *A61L 2/10* (2013.01); *A61M 25/0662* (2013.01); *A61M 2039/0273* (2013.01); *A61L 2202/11* (2013.01); *A61M 2039/0285* (2013.01); *A61L 2202/24* (2013.01); *A61M 25/0111* (2013.01); *A61M 2039/0279* (2013.01); *A61L 2202/14* (2013.01); *A61L 2/0047* (2013.01); *A61N 5/0601* (2013.01); *A61M 39/0247* (2013.01)
USPC .................................. 250/455.11; 250/454.11

(58) Field of Classification Search
CPC .................................................... A61N 5/0601
USPC ..................................................... 250/454.11
See application file for complete search history.

(56) References Cited

U.S. PATENT DOCUMENTS 3,931,518 A * 1/1976 Miller ....................... 250/227.24
4,411,655 A   10/1983 Schreck
(Continued)

FOREIGN PATENT DOCUMENTS

| WO | WO-2010/023329 A1 | 3/2010 |
| WO | WO-2010132429 A2 | 11/2010 |
| WO | WO-2010132429 A3 | 3/2011 |

OTHER PUBLICATIONS

"International Application Serial No. PCT/US2010/034362 Search Report mailed Jan. 25, 2011", 4.

(Continued)

*Primary Examiner* — Phillip A Johnston
*Assistant Examiner* — Sean Luck
(74) *Attorney, Agent, or Firm* — Schwegman Lundberg & Woessner, P.A.

(57) ABSTRACT

A device includes a sheath having a lumen defined by a wall. The wall has an outer surface that is configured to emit ultraviolet light in a direction substantially normal to the wall. The lumen has a distal end configured for percutaneous placement. The lumen has a proximal end configured to receive a catheter.

17 Claims, 5 Drawing Sheets

(56) References Cited

U.S. PATENT DOCUMENTS

| | | | |
|---|---|---|---|
| 4,634,146 A * | 1/1987 | Yaniv | 281/15.1 |
| 4,842,356 A * | 6/1989 | Mori | 606/15 |
| 4,906,238 A | 3/1990 | Greenfeld et al. | |
| 5,078,714 A * | 1/1992 | Katims | 606/38 |
| 5,260,020 A * | 11/1993 | Wilk et al. | 422/22 |
| 5,334,171 A | 8/1994 | Kaldany | |
| 5,470,330 A * | 11/1995 | Goldenberg et al. | 606/7 |
| 5,607,419 A | 3/1997 | Amplatz et al. | |
| 5,695,482 A | 12/1997 | Kaldany | |
| 6,302,898 B1 | 10/2001 | Edwards et al. | |
| 6,443,147 B1 * | 9/2002 | Matter | 128/200.26 |
| 6,461,569 B1 * | 10/2002 | Boudreaux | 422/24 |
| 6,551,346 B2 * | 4/2003 | Crossley | 607/88 |
| 7,041,121 B1 * | 5/2006 | Williams et al. | 607/89 |
| 7,367,342 B2 | 5/2008 | Butler | |
| 7,526,334 B2 * | 4/2009 | Herbst et al. | 604/20 |
| 2002/0065493 A1 | 5/2002 | Nyhart, Jr. | |
| 2003/0017073 A1 | 1/2003 | Eckhardt et al. | |
| 2004/0093044 A1 * | 5/2004 | Rychnovsky et al. | 607/88 |
| 2007/0073364 A1 * | 3/2007 | Meissner et al. | 607/88 |
| 2007/0176117 A1 | 8/2007 | Redmond et al. | |
| 2007/0282301 A1 * | 12/2007 | Segalescu et al. | 604/509 |
| 2008/0015661 A1 * | 1/2008 | Friedman et al. | 607/88 |
| 2008/0033519 A1 * | 2/2008 | Burwell et al. | 607/122 |
| 2008/0051736 A1 | 2/2008 | Rioux et al. | |
| 2008/0159908 A1 | 7/2008 | Redmond | |
| 2008/0255549 A1 * | 10/2008 | Rose et al. | 606/15 |
| 2008/0269846 A1 * | 10/2008 | Burwell et al. | 607/88 |

OTHER PUBLICATIONS

"Written Opinion Serial No. PCT/US2010/034362 Search Report mailed Jan. 25, 2011", 5.

"European Application Serial No. 10775386.5, Supplementary European Search Report mailed Nov. 2, 2012", 6 pgs.

"International Application Serial No. PCT/US2010/034362, International Preliminary Report on Patentability mailed Nov. 15, 2011", 7 pgs.

"International Application Serial No. PCT/US2010/034362, Written Opinion mailed Jan. 25, 2011", 5 pgs.

* cited by examiner

CATHETER INSERTION STERILIZATION

CLAIM OF PRIORITY

This application is a nationalization under 35 U.S.C. 371 of PCT/US2010/034362, filed May 12, 2010, published as WO 2010/132429, publication date Nov. 18, 2010, which claims the benefit of priority, under 35 U.S.C. Section 119(e), to Benjamin Arcand, U.S. Provisional Patent Application Ser. No. 61/177,042, entitled "CATHETER INSERTION STERILIZATION DEVICE," filed on May 11, 2009, both of which are incorporated herein by reference.

BACKGROUND

Infection at the point of insertion is associated with percutaneous insertion and placement of certain medical devices. Microbes, including bacteria, can be difficult to destroy and patients can become infected from various procedures.

SUMMARY

In a first example, a device includes a sheath having a lumen defined by a wall. The wall has an outer surface that is configured to emit ultraviolet light in a direction substantially normal to the wall. The lumen has a distal end configured for percutaneous placement. The lumen has a proximal end configured to receive a catheter.

In a second example, the proximal end is configured to couple with an ultraviolet lamp. In a third example including any of the proceeding examples, the proximal end is configured to couple with at least one light emitting diode (LED). In a fourth example including any of the proceeding examples, the wall is configured to emit ultraviolet light in a circumferential pattern. In a fifth example including any of the proceeding examples, the wall includes a light discharge port proximate the distal end and further including at least one optical passageway coupled to the discharge port. In a sixth example including any of the proceeding examples, the wall includes a side discharge lamp element, the lamp element is configured to generate the ultraviolet light. In a seventh example including any of the proceeding examples, the distal end includes a tapered profile. In an eighth example including any of the proceeding examples, the outer surface is patterned with a texture. In a ninth example including any of the proceeding examples, the wall includes an inner surface configured to emit ultraviolet light in a direction substantially normal to the wall. In a tenth example including any of the proceeding examples, the wall includes a first laminate and a second laminate separated by an air gap. In an eleventh example including any of the proceeding examples, the wall includes a light conductive polymer. In a twelfth example including any of the proceeding examples, the wall includes a plurality of prisms. In a thirteenth example including any of the proceeding examples, a user-operable control is coupled to the wall and configured to modulate emission of the ultraviolet light.

In a fourteenth example, a method includes forming a sheath. The sheath has a lumen defined by a wall. The wall has an outer surface configured to emit ultraviolet light in a direction substantially normal to the wall. The lumen has a distal end configured for percutaneous placement and has a proximal end configured to receive a catheter. The method includes coupling a light source with the sheath. The light source is configured to provide the ultraviolet light.

In a fifteenth example, forming the sheath includes forming a polymer sleeve. In a sixteenth example including any of the proceeding methods, coupling the light source includes coupling with at least one light emitting diode (LED). In a seventeenth example including any of the proceeding methods, forming the sheath includes configuring a distal end of the sheath to emit the ultraviolet light in a circumferential pattern. In an eighteenth example including any of the proceeding methods, forming the sheath includes forming at least one optical passageway in the wall. In a nineteenth example including any of the proceeding methods, forming the sheath includes forming a side discharge lamp element. In a twentieth example including any of the proceeding methods, forming the sheath includes at least one of forming a tapered profile or forming a patterned texture on the outer surface. In a twenty-first example including any of the proceeding methods, forming the sheath includes configuring an inner surface of the wall to emit ultraviolet light in a direction substantially normal to the wall. In a twenty-second example including any of the proceeding methods, forming the sheath includes forming a plurality of prisms.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
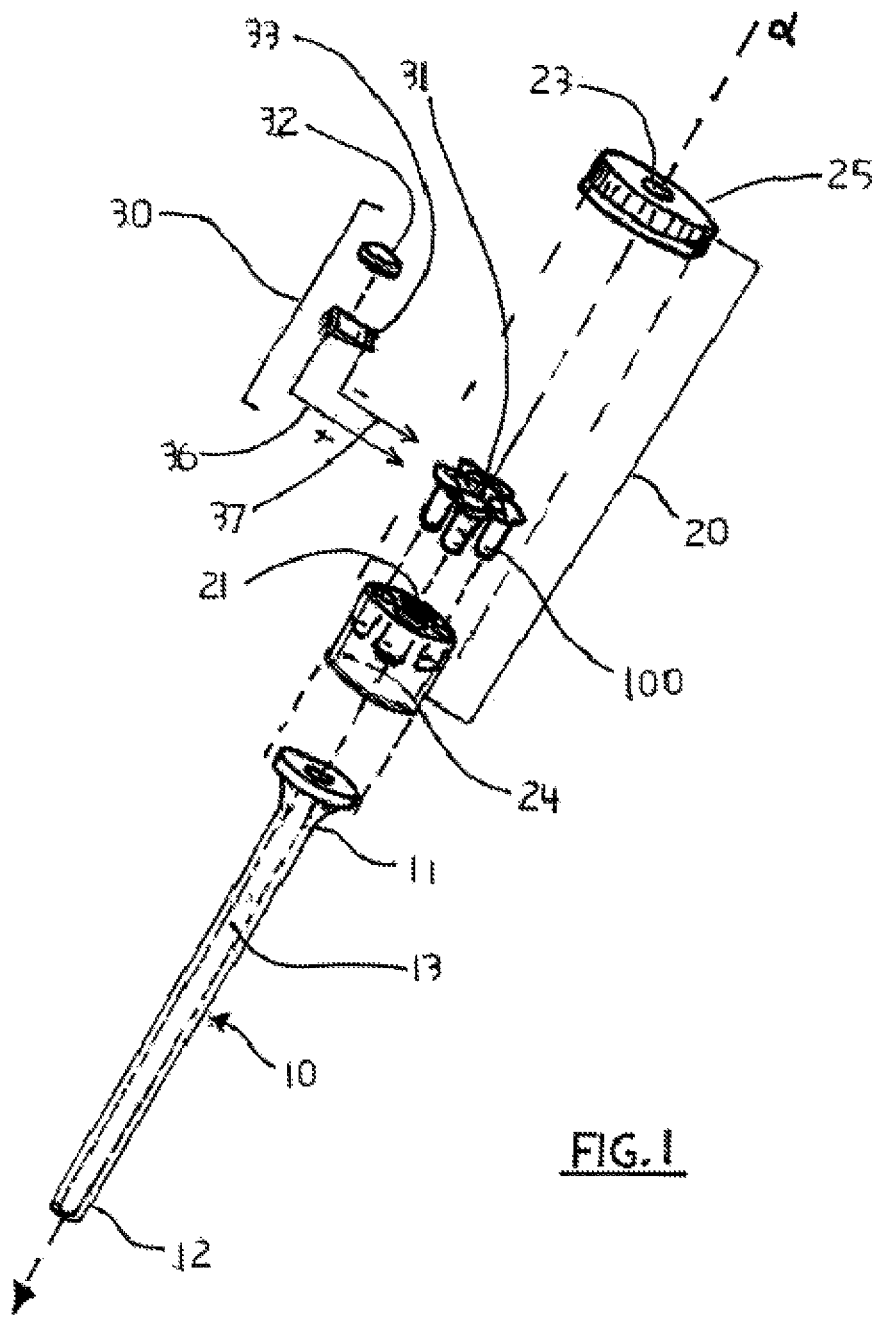
FIG. 1 includes a view of a device according to one example.

An example of the present subject matter includes an elongated catheter insertion device including an integrated ultraviolet (UV) sterilization system and configured to accommodate coaxial longitudinal insertion of an elongate instrument or device. A catheter introduction device can be fabricated to incorporate a UV sterilization assembly which provides sterilizing effects that are both inward-directed (toward the interior of the device and any instrument inserted through a central passageway) and outward-directed (toward the exterior of the device and toward the surrounding adjacent environment, e.g., tissue). One example can be configured for use with a long-term indwelling instrument and device which can benefit from ongoing or intermittent in situ sterilization, such as catheter placement and indwelling intubation procedures and equipment with relatively length residency in the patient.

One example includes a catheter insertion sterilization device including an elongate light transmission catheter sheath having a proximal end, a distal end, an exterior surface, and a lumen disposed longitudinally within. A lamp housing assembly is coupled to the proximal end of the sheath and includes a passageway within. An illumination assembly is positioned within the lamp housing assembly. The sheath lumen, the lamp housing assembly passageway, and the illumination assembly passageway share a common longitudinal axis and are configured to permit longitudinal coaxial insertion of a needle along the longitudinal axis.

One example includes a UV light source, a circuit, and a battery. The illumination assembly and light transmission catheter sheath components function in concert to subject any tool (such as a needle) inserted through the device to a sterilizing UV light prior to penetration into the tissue and vasculature of the patient. In addition, the device provides UV light for long-term, post-insertion, sterilization of the inserted instrument and the surrounding tissue and materials.

A device according to one example, is configured to cooperate with existing medical instruments, tools, devices, and equipment, such as needles and trocars, and provides supplemental sterilization of percutaneous devices immediately prior to and following tissue penetration.

When used in conjunction with pre-sterilization techniques and packaging, the present subject matter may reduce the likelihood of microbial introduction associated with percutaneous applications into the body, as well as reduce the likelihood of infection associated with long-term indwelling instruments and devices.

One example includes a catheter insertion sterilization device including an elongate light transmission catheter sheath having a proximal end and a distal end, an exterior surface, and lumen disposed longitudinally within, and an illumination assembly including a passageway and a circumscribing UV light source. The sheath lumen and illumination assembly simultaneously collectively sterilize both an instrument inserted into the device and tissue in contact with the exterior surface of the transmitting catheter sheath. In one example, the UV light source includes a LED and the light is in the UV-C band.

Some examples of the present subject matter are described relative to an intravenous catheter. A catheter can be used for a percutaneous procedure and in the context of this document, a catheter includes a variety of catheter devices. Examples of the present subject matter can include an insertion device such as a peritoneal dialysis catheter, an epidural catheter, a urological catheter, an optical or visualization instrument, and the like.

FIG. 1 illustrates a catheter insertion sterilization device comprising a light transmission catheter sheath 10, coupled to a lamp housing assembly 20 including an illumination assembly 30 within. The light transmission catheter sheath 10 can generally have an elongate configuration as illustrated. The elongate light transmission catheter sheath 10 can have a proximal end 11 and a distal end 12 and lumen 13 disposed longitudinally within. Lamp housing assembly 20 can be coupled to the proximal end 11 of the sheath 10 and can have a passageway 21 within.

In general, illumination assembly 30 can include passageway 30 there through and circumscribing light source, with the illumination assembly 30 positioned within the housing assembly 20. In one example, catheter sheath lumen 13 and the housing assembly passageway 21 and illumination assembly passageway 31 collectively share a longitudinal axis (represented in the figure by the symbol a) there through and are structured to permit longitudinal coaxial insertion of an instrument (such as a needle, not shown) along the shared longitudinal axis α of the assembled device.

In one example, the device, by way of this internalized illumination assembly 30, functions to generate a sterilizing light source. In one example, the light source includes a LED lamp unit. In the figure, multiple LED lamp units 100 are shown emitting a sterilizing UV frequency light. Sterilizing UV frequency light can include UV-A, UV-B, and UV-C frequency light.

In one example, the present subject matter is configured to direct a sterilizing light from lamp units 100 themselves (i.e., LEDs) inwardly directed toward the illumination assembly passageway 31 and instruments inserted there through (not shown), but alongside the catheter sheath lumen 13 and outwardly-directed sterilizing effect indirectly by transmission of the light through the catheter sheath material itself.

In one example, the elongate transmitting catheter sheath 10 includes a material that transmits the light throughout its length and surrounding the longitudinally inserted instrument or device (e.g., needle or trocar). In cooperation, the transmitting catheter sheath 10 complements the sterilizing effect together with the initial illumination assembly 30 light source. In one example, the surrounding tissue upon insertion of the device and transmitting catheter sheath 10 is also subjected to sterilizing UV light. Thus, the present subject matter provides multiple fronts of sterilizing treatment—both inward directed (toward the tool inserted through the lumen), and outward directed (toward the tissue immediately adjacent the exterior surface of the transmitting catheter sheath) during and after placement of the catheter in the patient.

Illumination assembly 30 can include passageway 31 and a circumscribing light source, and the illumination assembly 30 can be positioned within the lamp housing assembly 20. The circumscribing light source can be configured and structured by a variety of components and arrangements. For purposes of illustration, the circumscribing light source is depicted as a circular arrangement of a plurality (five) LED lamp units 100 surrounding and encircling a passageway 31. The number and arrangement of the light source can be different than that shown.

The extent and locations of the sterilizing light delivery can be varied and controlled by variations in the configuration of elements. In one example, the number and arrangement of elements is configured to deliver emitted light inward toward the instrument to be inserted through the sheath as well as transmit light through the catheter sheath material and exterior surface thereof.

Figure 2:
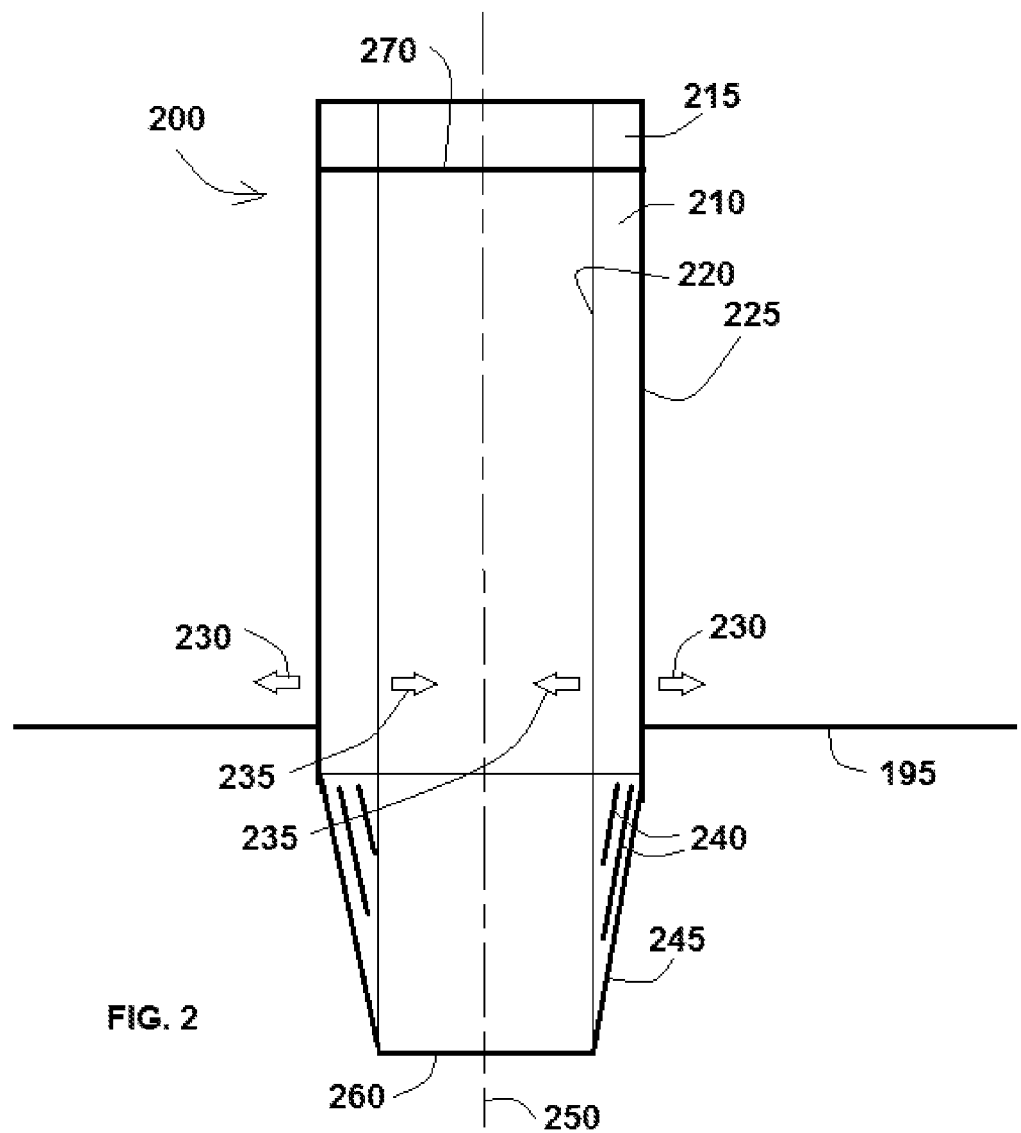
FIG. 2 includes a sheath according to one example.

FIG. 2 includes a view of sheath 200 according to one example. In this example, sheath 200 includes light source 215. Light source 215 can include one or more mercury light sources, or other light source configured to provide ultraviolet germicidal irradiation. Light source 215, in this example, is located near proximal end 270 of sheath 200. In one example, light source 215 includes a coupling configured to interface with an external UV hub. The external UV hub can include a light source with a coupling to a wave guide, an fiber optic element, or other energy conductor. In one example, a coupling (or connector) on the sheath is configured to connect with an external UV hub.

Sheath 200 includes a central lumen defined by wall 210 and aligned on axis 250. Wall 210, in the example illustrated is an annular structure in the form of a tube or sleeve. Wall 210 includes an inner surface 220 and an outer surface 225. Sheath 200 can have a fixed or variable overall length.

Ultraviolet light from light source 215 is carried through wall 210 and emitted from sheath 200 as shown by externally directed light arrows 230. Externally directed light is directed to bath the tissue surface 195 as well as the surrounding environment external to sheath 200.

In one example, ultraviolet light from light source 215 is carried through wall 210 and emitted from sheath 200 as shown by internally directed light arrows 235. Internally directed light is directed to bath interior regions of the lumen as well as any instrument or catheter (not shown in this view) inserted in the lumen. For example, an instrument or catheter can be manipulated within sheath 200 by movement (rotation or sliding) along axis 250.

Distal end 260 of sheath 200 is configured for percutaneous placement relative to the tissue as denoted by tissue surface 195. In the example shown, distal end 260 includes tapered profile 245. Tapered profile 245 can facilitate dilation of the tissue aperture and ease insertion and removal of sheath 200. Tapered profile 245 provide a non-uniform wall thickness.

Tissue surface 195 can include an aperture formed by a surgical procedure or a natural orifice. Examples can include a trancutaneous or percutaneous interface with an orifice. In various example, the present subject matter is configured for use with an endotracheal tube, a transcutaneous pin or wire (for external orthopaedic fixators), or a urinary catheter. Other examples are also contemplated.

Texture 240 is patterned on an external surface of sheath 200 in the region of the tapered profile 245. Texture 240 can include embossed or raised features that can be used to distribute ultraviolet light in a particular manner. For example, the ultraviolet light may be distributed on tissue surface 195 according to a predetermined gradient corresponding to the texture 240. In addition, texture 240 can ease installation and removal of sheath 200. In one example, texture 240 is omitted and the surface is substantially smooth.

Figure 3:
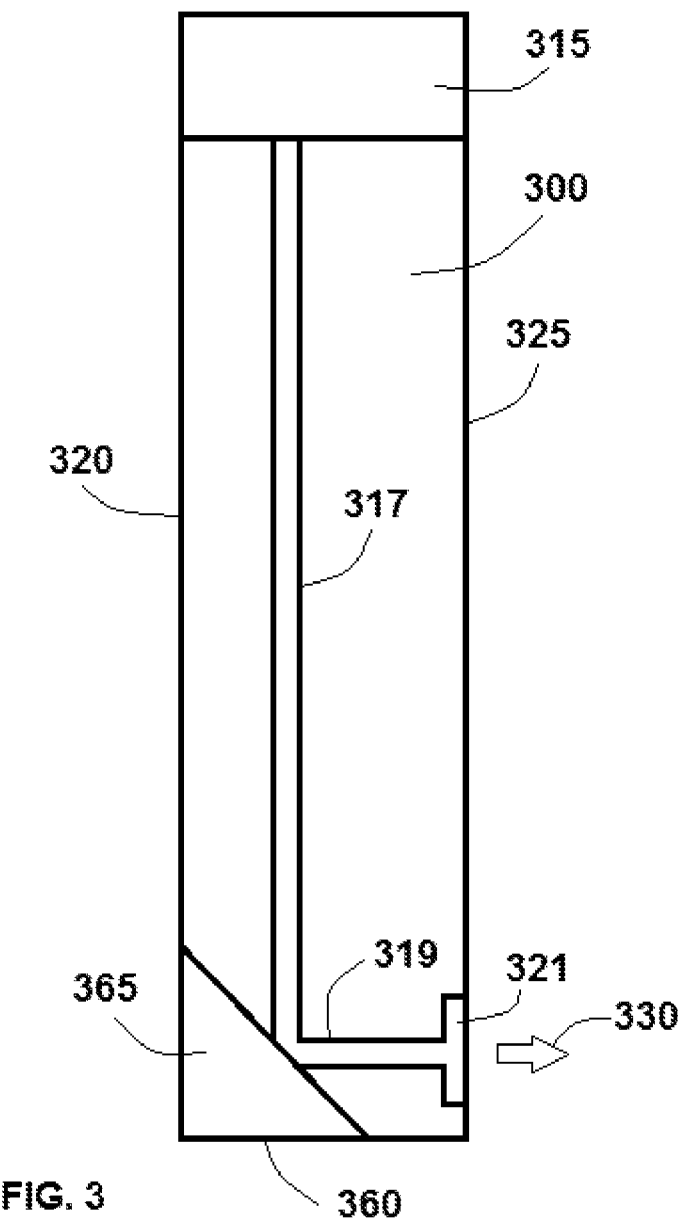
FIG. 3 includes a view of a portion of a sheath according to one example.

FIG. 3 includes a view of a portion of sheath 300 according to one example. This view illustrates an inner surface 320 and an outer surface 325 of a wall of sheath 300 in which the central axis is located to the left of sheath 300. Light source 315 is located at one end of sheath 300 and ultraviolet light is carried to distal end 360 by internal light passageway 317. Light conveyed by passageway 317 is reflected by a reflector, such as mirror 365, and directed to exit sheath 300 in a direction substantially normal to outer surface 325, as shown by arrow 330. Passageway 317 is coupled to passageway 319 which terminates in light channel 321. Light channel 321 is configured to distribute ultraviolet light externally and bath the surrounding environment with irradiation. In this example, UV light is transmitted from a source to a selected region of the surrounding environment.

FIG. 3 can also be viewed as depicting a laminated sheath 300. In this configuration, passageway 317 includes an air gap between an inner sleeve and an outer sleeve. The inner sleeve and outer sleeve are bonded at the ends of sheath 300. Passageway 317, as well as passageway 319 or light channel 321, can be fluid filled or include a medium selected to facilitate ultraviolet light transmission.

Figure 4:
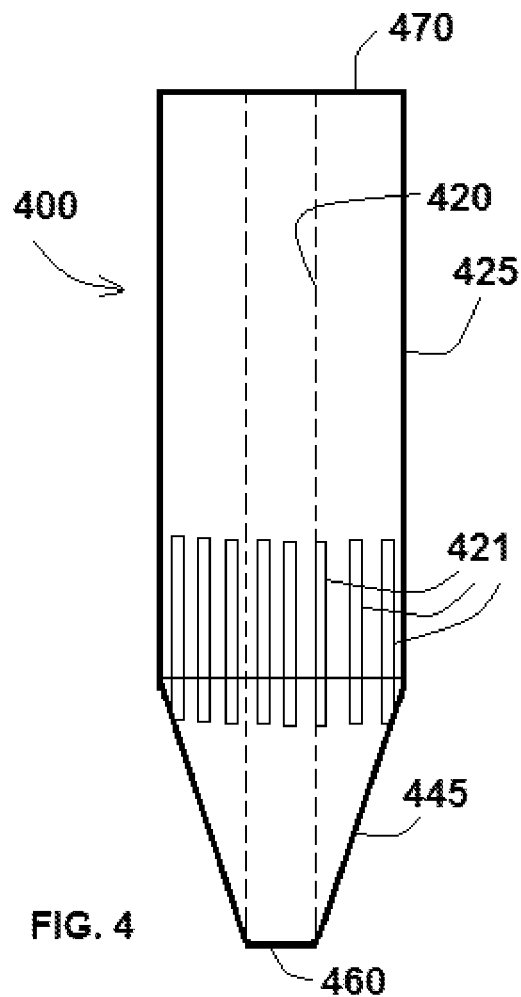
FIG. 4 includes a sheath according to one example.

FIG. 4 includes sheath 400 according to one example. Sheath 400 includes proximal end 470 and distal end 460. One or both of inner surface 420 and outer surface 425 are configured to emit ultraviolet light in a direction aligned substantially normal to the wall of sheath 400 as shown elsewhere in this document. Sheath 400 includes a plurality of light distribution channels 421 disposed on the outer surface 425. A light distribution channel 421, as shown, is configured to distribute light in a circumferential pattern about the axis of sheath 400. In this example, each light distribution channel 421 is independent of any other channel 421. In one example, the light is distributed through perforations or pores distributed about the outer surface 425. In one example, a light distribution channel 421 includes a side discharge light element. The light element can be generally linear, as shown, or can be a point source of light disposed on a surface or below a surface of sheath 400. In various example, the light element can be embedded in the wall of the sheath or disposed on a wall surface of the sheath.

The light distribution channels 421 shown in the figure are distributed on a uniform diameter portion of sheath 400 and distributed on the tapered profile portion 445 of sheath 400. In other examples, the light distribution channels 421 are located on one portion or the other. In addition, either one or both of the inner surface and outer surface can be smooth or can include a texture.

Figure 5:
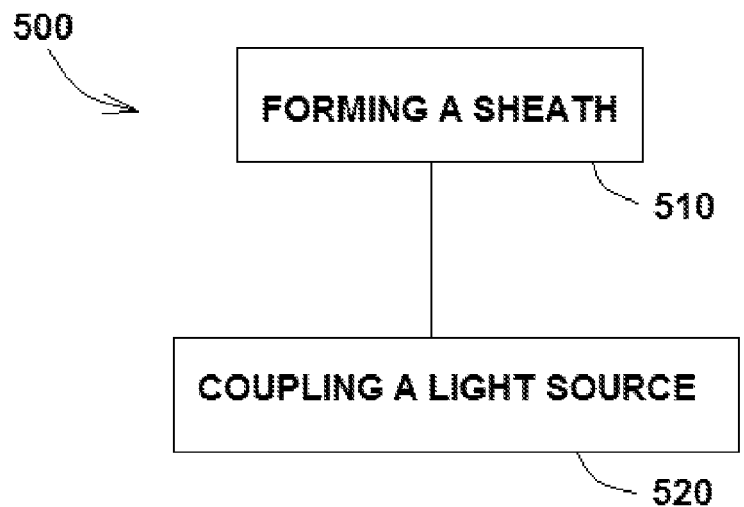
FIG. 5 includes a method according to one example.

FIG. 5 includes a flow chart illustrating method 500 according to one example. Method 500 includes, at 510, forming a sheath and, at 520, coupling a light source with the sheath. The sheath includes a lumen defined by a wall. The wall has an outer surface configured to emit ultraviolet light in a direction substantially normal to the wall. The lumen has a distal end configured for percutaneous placement and having a proximal end configured to receive a catheter. The sheath is coupled with a light source configured to provide the ultraviolet light.

Forming the sheath can include forming a polymer sleeve. In addition, forming the sheath can include molding, extruding, drawing, or other fabrication process. In some example, the sheath is fabricated of a polymer.

Coupling the light source can include coupling the sheath with at least one LED. An LED can be configured to emit ultraviolet irradiation suitable for reducing infection. In various example, coupling can include affixing an LED to a sheath or connecting an optical wave guide to the sheath.

Forming the sheath can include configuring a distal end of the sheath to emit the ultraviolet light in a circumferential pattern. This can include forming one or more light distribution channels, pores, aperatures or ports, for distributing light in a direction substantially normal to the sheath. The light can be distributed using a side discharge lamp element. Forming the sheath can include forming at least one optical passageway in the wall of the sheath. The passageway can be fabricated by removal of material or by providing a gap. The passageway can be filled with a gas or liquid selected to transmit the ultraviolet light.

Forming the sheath can include forming a tapered profile or forming a patterned texture on the outer surface of the sheath. The profile or texture can be configured to ease installation or removal, ease dilation of the tissue aperture, as well as reduce incidence of infection.

In one example, forming the sheath includes configuring an inner surface of the wall to emit ultraviolet light in a direction substantially normal to the wall. The inner surface can be configured with a side discharge light element or a light distribution channel in the manner described elsewhere in this document.

In one example, a surface (inner or outer) of the wall includes a plurality of prisms. The prisms can be formed on a sheet or in a tubular sleeve from which the sheath is formed. The prisms are configured to emit light in a direction substantially normal to the surface. In one example, the plurality of prisms are located on a first surface and an opposing surface includes a smooth surface. The prisms and the smooth surface are configured to reflect light from the wall to selected regions where infection may occur. As such, this example provides reflected light to the selected regions for germicidal purposes.

Figure 6:
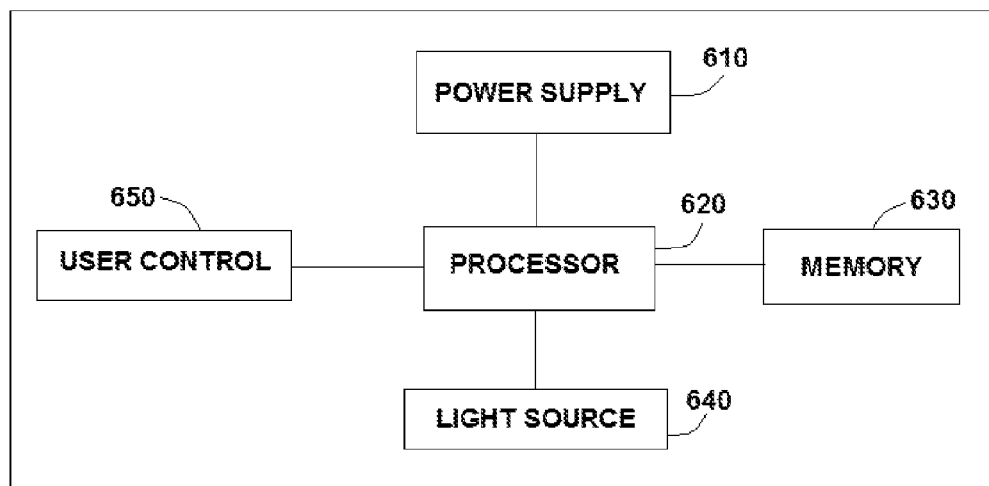
FIG. 6 includes a block diagram of a system according to one example.

FIG. 6 includes a block diagram of system 600 according to one example. System 600 includes power supply 610, processor 620, memory 630, light source 640, and user control 650. Power supply 610 can includes a metered line service or a portable supply such as a battery. Power supply 610 provides electric power for system 600 and, in the example illustrated, is coupled to processor 620. Processor 620 can include a microprocessor or computer and is configured to execute instructions stored on memory 630. Memory 630, also coupled to processor 620, can be configured to store data concerning system 600. Instructions in memory 630 can include, for example, code to control a duty cycle or otherwise modulate operation of light source 640. Light source 640, also coupled to processor 620, can include a mercury-based light source, an LED, or other source of ultraviolet energy.

User control 650 can include an electrical switch accessible to a user (such as a physician). User control 650 can include a switch located under a flexible membrane on a surface of a sheath.

ADDITIONAL NOTES

In addition to the example described above, other configurations are also contemplated. For example, the sheath can be configured for one-time use and after using the device, the sheath can be discarded. One example includes a sterilizable sheath that can be re-used following sterilization.

In addition, the sheath can be packaged as an integral unit with a catheter or other tool. The catheter or other tool can be configured for a close wall fit on the interior or can be configured to facilitate ultraviolet germicidal irradiation. The catheter can be held captive in the sheath by corresponding features or the catheter and sheath can be configured for separability. In one example, the sheath includes a lumen configured to receive a variety of different catheters or other tools and having different functions and sizes.

The catheter can be held in position with the sheath by a snap fit feature, a threaded feature, or a twist-lock feature.

The punctured tissue site may be prone to infection by a catheter, such as an indwelling catheter. The present subject matter includes a sheath that can be disposed at the interface between the catheter and the tissue. The sheath is configured to irradiate the interface (with the tissue external to the sheath and with the catheter internal to the sheath) using UV sterilizing light energy. The UV sterilizing light energy is configured to reduce or kill infectious microbes and destroy colonies that may impair health.

In one example, the sheath facilitates dilation and placement of a catheter. The sheath includes a lumen configured to accommodate various interventional devices.

The sheath in one example is configured as a light pipe. As such, UV light at one end is transmitted to another end where it is distributed at regions where infection may occur. The light can be distributed in a uniform pattern or distributed in a gradient pattern selected according to likelihood of infection or based on other criteria.

In one example, the ultraviolet light is provided by a light source in a lamp housing. The light source can include an LED or an externally-supplied light source coupled by a fiber optic cable or wave guide.

Ultraviolet germicidal irradiation, according to an example of the present subject matter, can be provided by a low pressure mercury vapor discharge tube. Shortwave UV light can be used for sterilizing microbiological contaminants from an irradiated surface.

Ultraviolet light includes electromagnetic radiation with wavelengths shorter than visible light. Ultraviolet light can be separated into various ranges, with short range UV (UVC) sometimes referred to as "germicidal UV." At certain wavelengths UV is mutagenic to bacteria, viruses and other micro-organisms. At a wavelength of 2,537 Angstroms (254 nm), UV will break the molecular bonds within micro-organismal DNA, producing thymine dimers in their DNA thereby destroying them, rendering them harmless or prohibiting growth and reproduction. According to one example, a low-pressure mercury-vapor lamp will emit a substantial portion of light at about 254 nanometers (nm). Other wavelengths are also suitable, such as about 265 nm and about 185 nm.

Various types of germicidal lamps can be used with the present subject matter. For example, a low-pressure UV lamp can provide approximately 1 W/cm$^3$ power density.

Another example is an amalgam UV lamp which as a power density of approximately 2-3 W/cm$^3$. A medium-pressure UV lamp can also be used. In one example, a pulsed surface discharge (SD) lamp can be used to disinfect.

In an SD lamp, a high-power electrical pulse is discharged along the surface of a dielectric substrate, generating a light-emitting plasma along its surface. The SD lamp is free of mercury and has a higher inherent UV efficiency than a medium-pressure mercury lamp.

In one example, the sheath includes a biocompatible polymer that permits UV transmittance. In addition, the sheath is configured with a suitable angle at which to direct the LEDs into the sleeve for UV transmittance.

The sheath material can be selected based on UV transmittance characteristics. For example, a short wavelength of light can be communicated using a polymer or a quartz material that does not absorb photons and improves light transmittance.

One example includes a catheter insertion sterilization device including an elongate light transmission catheter sheath having a proximal end and a distal end and a lumen running longitudinally within. The example includes a lamp housing assembly coupled to the proximal end of the sheath and having a passageway within. The example includes an illumination assembly having a passageway and a circumscribing light source. The illumination assembly is positioned within the lamp housing assembly. The sheath lumen, the housing assembly passageway and the illumination assembly passageway collectively share a longitudinal axis there through and are configured to permit longitudinal coaxial insertion of an instrument through the assembled device.

In one example, the illumination assembly includes a sterilizing light source. In one example, the sterilizing light source includes at least one LED lamp unit that emits UV frequency light. The UV frequency light is selected from UV-A, UV-B, and UV-C frequency light. The light transmission catheter sheath includes a transparent flexible polymer.

One example includes a catheter insertion sterilization device including an elongate light transmission catheter sheath having a proximal end and a distal end, an exterior surface, and a lumen running longitudinally within. The illumination assembly includes a passageway and a circumscribing sterilizing light source. The sheath lumen and illumination assembly simultaneously collectively sterilize both an instrument inserted through the device and tissue immediately adjacent to the exterior surface of the transmitting catheter sheath.

As used herein, the term percutaneous denotes through the skin or through an orifice (including surgically formed or naturally occurring) and includes the term transcutaneous. In addition, the term catheter denotes tubular as well as solid material (such as a fixation pin).

Ultraviolet light can be used to sterilize. The UV light can be classified as UV-A, UV-B, or UV-C, any of which can be used in an example of the present subject matter. Light having a wavelength in the range of 300-400 nm is deemed UV-A and can be generated using a suitable LED.

In one example, the wall of the sheath includes an optical fiber. The optical fiber can be configured to carry UV light.

In one example, the sheath is configured to carry the catheter (or other tool) on an axis eccentric relative to the center axis of the sheath. For example, the sheath can be configured to carry multiple catheters on different axes, any one of which can be offset relative to the sheath center.

In addition, the UV light can be carried in the sheath in a passageway that is eccentric relative to the center axis of the sheath. For example, UV light may be transmitted in a fiber optic pathway offset from the sheath centerline. Furthermore, the light emitted by the sheath can be distributed in an asymmetrical or offset pattern.

The light source can be coupled to an end of the sheath as illustrated in FIG. 1 and FIG. 2. In addition, the light source can be coupled to a side portion of the sheath. As such, UV light can be transmitted through a wall surface (normal to the sheath axis or angled relative to the sheath axis) and carried to the distal portion for distribution. By way of examples, the UV light can be coupled to the sheath at a specific segment of the circumference of the sheath or the UV light can be coupled to fully encircle the circumference of the sheath. In addition, UV light distributed internal to the sheath can be distributed at any location throughout the length of the lumen.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus for sterilizing one or both of a medical device and bodily tissue adjacent to the medical device, comprising:
    a cylindrical sheath, extending from a sheath proximal end to a sheath distal end, including a sheath wall defining a sheath lumen, the sheath wall and the sheath lumen capable of receiving and transmitting a sterilizing light, wherein the sheath wall includes at least one channel comprising a longitudinal portion and a transverse portion, extending in a direction transverse to the longitudinal portion, the transverse portion including a port formed in an inner surface of the sheath wall, adjacent the sheath lumen, or an outer surface of the sheath wall;
    a housing, surrounding the sheath proximal end, including a housing outer wall and a housing inner wall, the housing outer wall and housing inner wall defining a housing chamber there between, the housing inner wall defining a housing lumen, wherein the housing lumen and the sheath lumens are collinear and configured to receive a portion of the medical device; and
    a sterilizing assembly including a light source electrically coupled to a battery, the light source and the battery located within the housing chamber.

2. The apparatus of claim 1, wherein the at least one channel includes a reflector to direct light to the port.

3. The apparatus of claim 1, wherein the at least one channel includes air, a light conductive polymer, a light conductive gas, or a light conductive fluid.

4. The apparatus of claim 1, wherein the sheath wall comprises an outer surface and an inner surface, at least one of the outer surface and the inner surface includes a raised or embossed pattern formed therein and configured to disperse light in a dispersion pattern corresponding to the raised or embossed pattern.

5. The apparatus of claim 1, wherein the sheath wall includes an outer surface and an inner surface, at least one of the outer surface and the inner surface includes a plurality of distribution channels formed therein, the plurality of distribution channels configured to circumferentially disperse light.

6. A method of manufacturing a sterilization apparatus, comprising:
    forming or obtaining a cylindrical sheath extending from a proximal end to a distal end, including forming or obtaining a sheath wall configured to receive and transmit a sterilizing light and defining a sheath lumen, the sheath wall including at least one channel comprising a longitudinal portion and a transverse portion, extending in a direction transverse to the longitudinal portion, the transverse portion including a port formed in an inner surface of the sheath wall, adjacent the sheath lumen, or an outer surface of the sheath wall;

forming or obtaining an integrated, stand-alone illumination assembly comprising a housing, including a housing chamber and a housing lumen, and a sterilization assembly disposed in the housing chamber, the sterilization assembly including a light source electrically coupled to a battery; and coupling the illumination assembly to the proximal end of the sheath, including aligning the sheath lumen and the housing lumen such that the sheath lumen and the housing lumen are collinear and configured to receive a portion of a medical device.

7. The method of claim 6, wherein forming the sheath includes forming at least one channel within the sheath wall, the at least one channel including air, a light conductive gas, a light conductive fluid, or a light conductive material other than a fiber optic cable.

8. The method of claim 6, wherein forming the sheath includes forming a polymer to simultaneously transmit light in a direction inward, toward the sheath lumen, and outward, away from the sheath lumen.

9. A method for sterilizing a medical device and a bodily tissue adjacent to the medical device, comprising:

providing or obtaining a cylindrical sheath having a sheath proximal end and a sheath distal end, and including a wall configured to receive and transmit a sterilizing light and defining a sheath lumen, the sheath wall including at least one channel comprising a longitudinal portion and a transverse portion, extending in a direction transverse to the longitudinal portion, the transverse portion including a port formed in an inner surface of the sheath wall, adjacent the sheath lumen, or outer surface of the sheath wall;

coupling an illumination assembly to the sheath proximal end, the illumination assembly comprising a housing, including a housing chamber and a housing lumen, and a sterilizing light source electrically coupled to a battery and disposed within the housing chamber, wherein the housing lumen is collinear with the sheath lumen when the housing illumination assembly is coupled to the sheath proximal end;

receiving a portion of a medical device within the housing lumen and within at least a portion of the sheath lumen; and transmitting a sterilizing light from the sterilizing light source through the wall in a direction substantially normal to the wall.

10. The method of claim 9, wherein the step of receiving includes advancing the medical device through the sheath lumen from the sheath proximal end to the sheath distal end and into a bodily tissue or a bodily orifice or cavity.

11. A method for sterilizing a medical device and a bodily tissue adjacent to the medical device, comprising:

providing or obtaining a cylindrical sheath having a sheath proximal end and a sheath distal end, and including a wall configured to receive and transmit a sterilizing light and defining a sheath lumen, the sheath wall including at least one channel comprising a longitudinal portion and a transverse portion, extending in a direction transverse to the longitudinal portion, the transverse portion including a port formed in an inner surface of the sheath wall, adjacent the sheath lumen, or an outer surface of the sheath wall;

inserting at least the distal end of the sheath into a bodily tissue or a bodily orifice or cavity;

receiving a portion of a medical device within at least a portion of the sheath lumen;

coupling an illumination assembly to the sheath proximal end, the illumination assembly comprising a housing, including a housing chamber and a housing lumen, and a sterilizing light source electrically coupled to a battery and disposed within the housing chamber, wherein the housing lumen is collinear with the sheath lumen when the housing illumination assembly is coupled to the sheath proximal end; and transmitting a sterilizing light from the sterilizing light source through the sheath wall in a direction substantially normal to the wall.

12. The method of claim 11, wherein the step of receiving includes advancing the medical device through the sheath lumen to the sheath distal end and into a bodily tissue or into a bodily orifice or cavity.

13. A sterilization system, comprising:

a cylindrical sheath, extending from a sheath proximal end to a sheath distal end, including a sheath wall configured to receive and transmit a sterilizing light and defining a sheath lumen, the sheath wall including at least one channel comprising a longitudinal portion and a transverse portion, extending in a direction transverse to the longitudinal portion, the transverse portion including a port formed in an inner surface of the sheath wall, adjacent the sheath lumen, or an outer surface of the sheath wall; and an integrated, stand-alone illumination assembly configured to be removably coupled to the sheath proximal end, the illumination assembly comprising:

a housing, including a housing chamber and a housing lumen; and a sterilizing light source electrically coupled to a battery and disposed within the housing chamber, the housing lumen configured to be collinear with the sheath lumen when the housing illumination assembly is coupled to the sheath proximal end.

14. The system of claim 13, the sheath wall including at least one channel formed within the sheath wall, the at least one channel including air, a light conductive polymer, a light conductive gas, or a light conductive liquid.

15. The system of claim 13, wherein the sheath wall comprises an outer surface and an inner surface, at least one of the outer surface and inner surface includes a raised or embossed pattern formed therein to disperse light in a dispersion pattern corresponding to the raised or embossed pattern.

16. The system of claim 13, wherein the sheath wall includes an outer surface and an inner surface, a plurality of pores are formed in at least one of the outer surface or the inner surface, the plurality of pores configured to circumferentially disperse light.

17. The system of claim 13, wherein the sterilizing light source comprises a plurality of lamps configured to emit a sterilizing light.

* * * * *